US00PP31558P3

(12) United States Plant Patent
Dirr et al.

(10) Patent No.: US PP31,558 P3
(45) Date of Patent: Mar. 17, 2020

(54) CRAPEMYRTLE PLANT NAMED 'DJ 06-14'

(50) Latin Name: ***Lagerstroemia* hybrid**
Varietal Denomination: 'DJ 06-14'

(71) Applicant: University of Georgia Research Foundation, Inc., Athens, GA (US)

(72) Inventors: Matthew A. Dirr, Watkinsville, GA (US); Donglin Zhang, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/350,967

(22) Filed: Feb. 5, 2019

(65) Prior Publication Data

US 2019/0246543 P1 Aug. 8, 2019

Related U.S. Application Data

(60) Provisional application No. 62/627,070, filed on Feb. 6, 2018.

(51) Int. Cl.
*A01H 5/00* (2018.01)
*A01H 6/00* (2018.01)
*A01H 5/02* (2018.01)

(52) U.S. Cl.
USPC ..... Plt./252
CPC ..... *A01H 6/00* (2018.05); *A01H 5/02* (2013.01)

(58) Field of Classification Search
USPC ..... Plt./252
CPC ..... A01H 5/00
See application file for complete search history.

*Primary Examiner* — Annette H Para

(74) *Attorney, Agent, or Firm* — Klarquist Sparkman, LLP

(57) ABSTRACT

A new crapemyrtle plant has deep, uniform purple foliage and stems; a deep raspberry pink/red flower color; an intermediate upright growth habit; and powdery mildew and *Cercospera* resistance.

2 Drawing Sheets

Latin name of the genus and species of the plant claimed: 'DJ 06-14' is a Crapemyrtle plant that is a *Lagerstroemia* hybrid.

Variety denomination: The new crapemyrtle plant claimed is a variety denominated 'DJ 06-14'.

BACKGROUND OF THE INVENTION

The present invention relates to the discovery of a new and distinct cultivar of the ornamental flowering shrub *Lagerstroemia indica* x *Lagerstroemia fauriei*, commonly known as crapemyrtle, and hereafter referred to by the varietal denomination 'DJ 06-14', as herein described and illustrated.

The new crapemyrtle originated from open pollinated seed of a patented plant, 'Chocolate Mocha' Crapemyrtle (U.S. Plant Pat. No. 21,540). 'DJ 06-14' was selected from plants grown at a horticultural farm in Watkinsville, Ga. The seedlings were planted in containers and selections were made for plants based on the following criteria:

1.) Intermediate, upright growth habit
2.) Powdery mildew resistance
3.) Flower color and quality
4.) Deep purple foliage and stem color 'DJ 06-14' was selected in September 2014.

Asexual reproduction by traditional vegetative cuttings since 2014 at the Horticulture Farm in Watkinsville, Ga. has shown that the distinguishing characteristics of the new crapemyrtle variety, 'DJ 06-14' are stable and reproduced true to type in successive generations.

SUMMARY OF THE INVENTION

'DJ 06-14' has not been observed under all possible environmental conditions. The phenotype may vary somewhat with changes in light, temperature, soil and rainfall amount, however, any variance in genotype.

The following traits have been observed and represent the characteristics of the new cultivar. Asexual propagation by cuttings has proven that these characteristics are firmly fixed in succeeding asexually propagated generations. In combination, these characteristics distinguish 'DJ 06-14' from all other varieties known to the inventor:

1.) Deep, uniform, purple foliage and stems;
2.) Deep raspberry pink/red flower color;
3.) Intermediate, upright growth habit; and
4.) Powdery mildew and *Cercospera* resistance.

'DJ 06-14' is distinguished from its parent plant *Lagerstroemia indica* x *Lagerstroemia fauriei* 'Chocolate Mocha' by its improved, more consistent, deeper purple foliage and its larger, raspberry pink/red flower color. 'DJ 06-14', after 3 years of evaluation, has proven to be more resistant to powdery mildew and *Cercospera* than 'Chocolate Mocha'.

DESCRIPTION OF THE DRAWINGS

The accompanying colored photographic illustrations show the overall appearance and distinct characteristics of the new 'DJ 06-14' cultivar. The colors in the photographs are as close as possible with the photographic and printing technology utilized.

DETAILED DESCRIPTION

Figure 1:
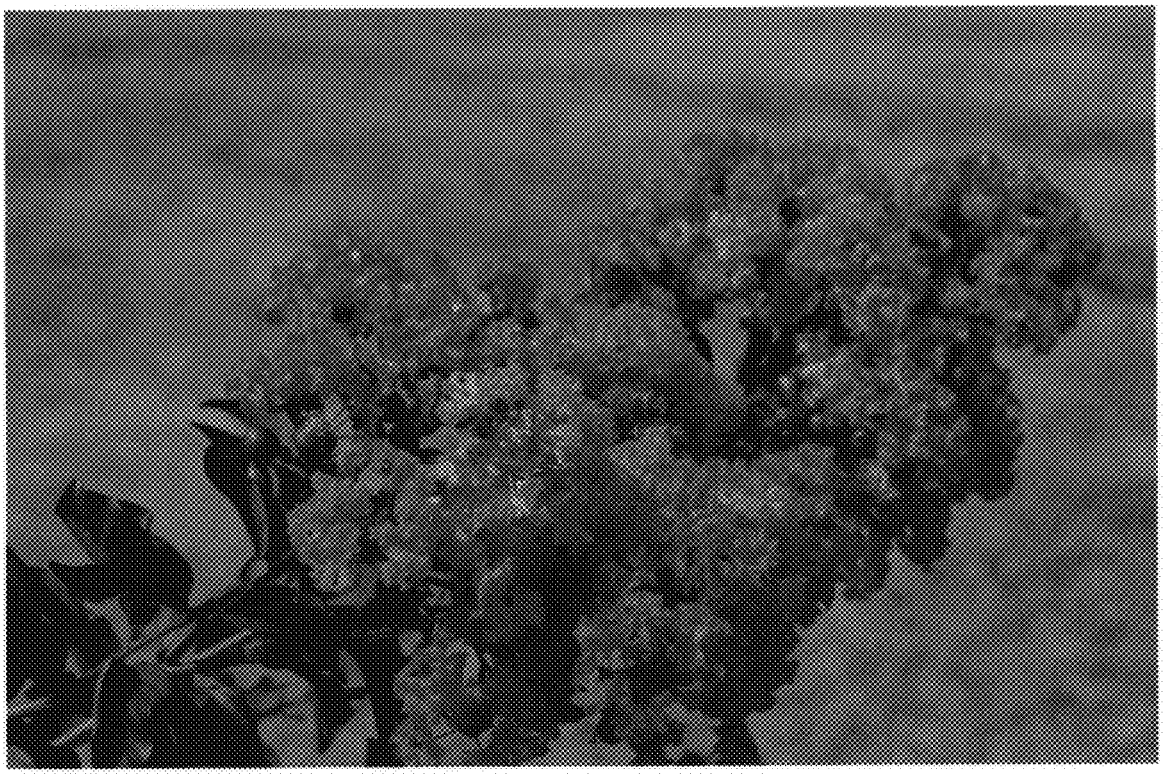
FIG. 1 is a close up view of the flowers of the 'DJ 06-14' variety.
Figure 2:
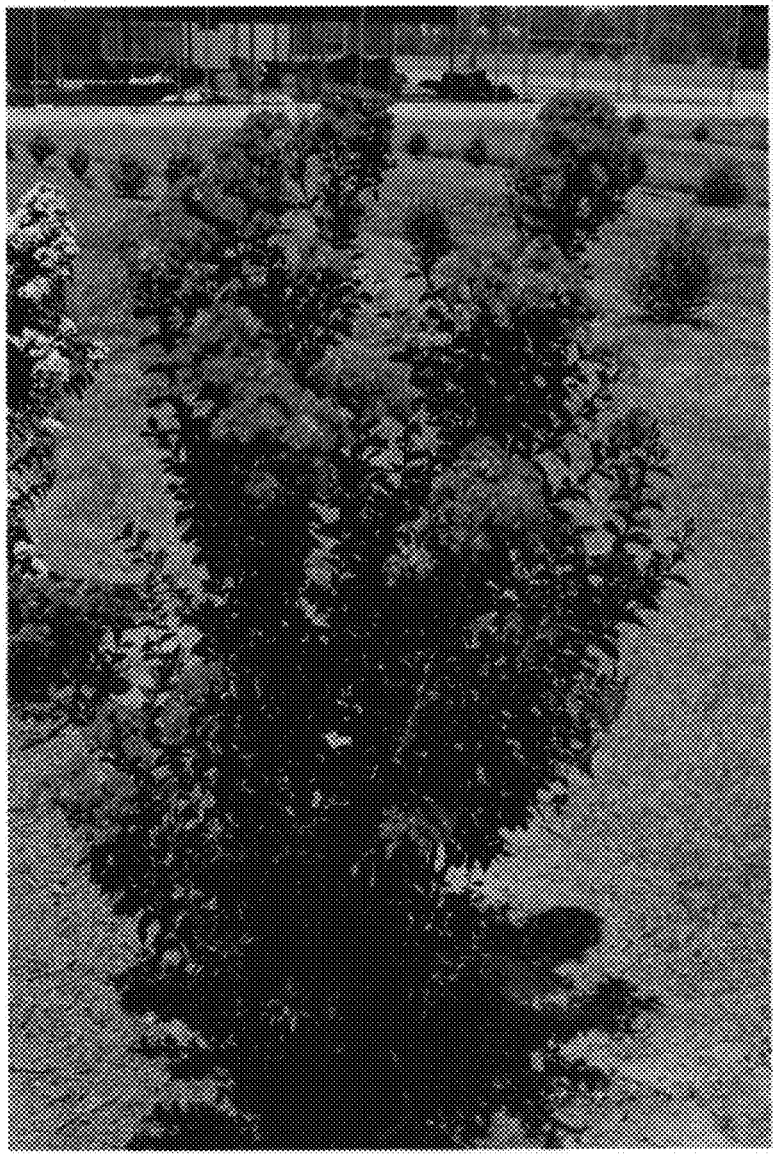
FIG. 2 is a view of a flowering 'DJ 06-14' plant.

In the following description, color references are made to The Royal Horticulture Society Colour Chart, 2015 Edition, except where general terms of ordinary dictionary significance are used. Plants used for the description were approximately 2.5 years old and grown in 11.4 liter containers in full sun at the horticultural farm in Watkinsville, Ga.

Botanical/plant description: 'DJ 06-14' is a cultivar of *Lagerstroemia indica* x *Lagerstroemia fauriei* 'Chocolate Mocha'. The current variety is a progeny from seed collected from 'Chocolate Mocha' in November of 2013. Male, or pollen parent is unknown (open-pollinated).

*General description*.—Flowering shrub; compact, upright, intermediate growth habit. Freely branching; lateral branches abundant without pruning (although some winter pruning of dead wood is recommended). Ultimately, proper pruning will result in a fine-textured, dense habit.

*Plant size*.—The original plant has been in the ground for 3.5 years, is 152 cm high from the soil level to the top of the uppermost inflorescences and about 91 cm wide.

*Blooming period*.—June-September in Watkinsville, Ga. Rebloom after 6-8 weeks when spent flower are removed.

*Plant type*.—Deciduous flowering shrub.

*Plant habit*.—Compact, branching, upright in outline, finely textured, freely branched without pruning. Height and spread, about 2.4 meters in height and 1 meter in width.

*Cold hardiness*.—USDA zones 6-8.

*Disease*.—Resistant to powdery mildew (caused by *erysiphe Lagerstroemiae*) and *cercospera* leaf spot (*cercospera lythracearum*) have been observed.

*Root description*.—Numerous fibrous and well branched, color 155D; young roots are fibrous and old roots are woody.

*Root development*.—Average 6 weeks at 25 degrees C. for root initiation and average 3 months at 30 degrees C. to produce a young rooted plant.

*Propagation*.—Vegetatively propagated from cuttings, softwood stem cuttings root readily at 20-25 degrees C. Growth rate is moderate.

Branch description:

*Branch shape*.—Tetragonal on first year growth, round on second year growth.

*Branch color*.—First year N79B; Second year 199D; trunk is 199E.

*Branch size*.—Main branch: first year 30 cm in length and 5 mm in diameter; Second year 60 cm in length and 8 mm in diameter, lateral branches are 60-70 cm in length and 1.5 cm in diameter, Trunk; multi branched and 2.5 cm in diameter at the soil level.

*Branch surface*.—Lateral branches sparsely covered with irregular lenticals 177B in color, trunk fine, smooth barked.

*Branch strength*.—Young; flexible but strong, mature; easily snapped.

*Branching*.—Freely branching habit without pruning, average of 8 lateral branches.

*Branching aspect*.—Held at angles between 30 to 60 degrees, internode length average at 2 cm.

*Vegetative buds*.—Alternate sub-opposite in arrangement, average of 4 mm in length and 3 mm in width, conical in shape 5-scaled imbricate and lack pubescence, color N79B.

Foliage description:

*Leaf shape*.—Obvate to elliptical, leaf division is single (simple).

*Leaf base*.—Cuneate.

*Leaf apex*.—Acute to abruptly acuminate.

*Leaf veination*.—Pinnate, upper surface color N186A, lower surface color N187D.

*Leaf margins*.—Entire.

*Leaf arrangement*.—Sub-opposite to alternate.

*Leaf attachment*.—Petiolate.

*Leaf surface*.—Upper surface glossy; lower surface dull, slightly pubescent.

*Leaf size*.—Average 5 cm in length and 2.5 in width.

*Leaf quantity*.—Average 76 per lateral branch.

*Leaf color*.—Young upper surface N186A, young lower surface N187B; mature upper surface N186A, mature lower surface N187B.

*Petiole*.—Average 1 mm in length and 1 mm in diameter, surface texture smooth; color N186B, moderate strong.

Flower description:

*Inflorescence type*.—Terminal panicle.

*Thyrses*.—Number — 18; shape — broad pyramidal.

*Persistence of inflorescence*.—Inflorescence are showy for an average of 4 weeks, individual flowers persist for an average of 2 days, self cleaning.

*Inflorescence size*.—An average of 20 cm in height 15 cm in width.

*Inflorescence number*.—Terminally borne, 1 per lateral branch.

*Flower number*.—Average of 100-200 flowers and flower buds per inflorescence.

*Flower fragrance*.—Light sweet scent.

*Flower buds*.—Globose in shape, an average of 7 mm in length and depth, rounded apex, surface is lustrous with 6 distinct suture lines, color 183B.

*Flower aspect*.—Upright to outward.

*Flower type*.—Actinomorphic.

*Flower size*.—Average of 2 cm in height and 4 cm in diameter.

*Petals*.—Typically 6, rotate/whorled in arrangement, fan shaped, rounded, ruffled margins, sagittate base, ruffled and rounded apex. Both surfaces glabrous. Typical petals have a length of about 0.5 mm and a width of about 10 mm and have a fine texture. Color when opening, and when fully opened upper and lower surfaces; 63A.

*Sepals*.—Six sepals fused at the base; typical length 7 mm, typical width 10 mm; glabrous on both surfaces; acuminate, entire, fine texture, sagittate base; ruffled and rounded apex.

*Calyx*.—Consists of 6 sepals fused at base, acute apices an average of 1 cm in length and 1 cm in diameter color on both surfaces 183D, smooth and glabrous on both surfaces.

*Peduncle*.—Strong, average 7 cm in length and 3 mm in diameter. Color N186C. surface is covered with fine, appressed pubescence and is strong.

*Pedicels*.—Strong, average of 8 mm in length and 1 mm in diameter, color N186C. surface is covered with fine appressed pubescence.

Reproductive organs:

*Stamens*.—25-30 stamens clustered in the center. 6 mm in length surrounded by 6 longer stamens, 1 cm in length, glabrous, surface, anthers; 12A color.

*Pistils*.—Single(1) Average of 2 cm in length and width, style; 1.5 cm in length and 59D in color, stigma; rounded less than 1 mm in diameter 59D in color, ovary; superior, 157C in color. 3 mm in diameter.

Fruit and seed:

*Fruit*.—Capsule; 6 valved dehiscent; oval rounded in shape; typical diameter about 9 mm; typical length about 1.1 mm. Immature 141C in color, mature N199C in color; fruit depression at apex — absent; fruit depression at base — absent.

*Seeds*.—Each capsule contains 25 seeds on average, 6mm in length and 3 mm in width and N199B in color.

We claim:

1. A new and distinct cultivar of the Crapemyrtle plant named 'DJ 06-14', as herein illustrated and described.

* * * * *